US012310785B2

(12) United States Patent
Lee et al.

(10) Patent No.: US 12,310,785 B2
(45) Date of Patent: May 27, 2025

(54) ULTRASOUND IMAGING DEVICE AND ULTRASOUND IMAGE GENERATION METHOD FOR IDENTIFYING DEGREE OF DELIVERY PROGRESS OF FETUS

(71) Applicants: SAMSUNG MEDISON CO., LTD., Gangwon-do (KR); KOREA UNIVERSITY RESEARCH AND BUSINESS FOUNDATION, Seoul (KR)

(72) Inventors: Dongeun Lee, Seongnam-si (KR); Jinyoung Lee, Seongnam-si (KR); Minjeong Oh, Seoul (KR); Geumjoon Cho, Seoul (KR); Hyejin Choi, Seoul (KR)

(73) Assignees: SAMSUNG MEDISON CO., LTD., Gangwon-do (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 466 days.

(21) Appl. No.: 17/422,079

(22) PCT Filed: May 15, 2019

(86) PCT No.: PCT/KR2019/005836
§ 371 (c)(1),
(2) Date: Jul. 9, 2021

(87) PCT Pub. No.: WO2020/159008
PCT Pub. Date: Aug. 6, 2020

(65) Prior Publication Data
US 2022/0096046 A1    Mar. 31, 2022

(30) Foreign Application Priority Data
Jan. 30, 2019    (KR) .................. 10-2019-0011984

(51) Int. Cl.
*A61B 8/08* (2006.01)
*A61B 8/00* (2006.01)
*A61B 8/14* (2006.01)

(52) U.S. Cl.
CPC .......... *A61B 8/0866* (2013.01); *A61B 8/0875* (2013.01); *A61B 8/14* (2013.01); *A61B 8/463* (2013.01)

(58) Field of Classification Search
CPC ....... A61B 8/0866; A61B 8/0875; A61B 8/14; A61B 8/4405; A61B 8/4427;
(Continued)

(56) References Cited

U.S. PATENT DOCUMENTS 5,740,266 A * 4/1998 Weiss ................. G06T 7/64
382/256
7,850,625 B2 * 12/2010 Paltieli ................ G06T 7/12
600/443
(Continued)

FOREIGN PATENT DOCUMENTS

JP    S63-305839 A    12/1988
JP    3474584 B2    9/2003
(Continued)

OTHER PUBLICATIONS

Extended European Search Report dated Sep. 22, 2022 issued in European Patent Application No. 19912750.7.
(Continued)

*Primary Examiner* — Chao Sheng
*Assistant Examiner* — Maria Christina Talty
(74) *Attorney, Agent, or Firm* — Morgan Lewis & Bockius LLP

(57) ABSTRACT

The present disclosure discloses an ultrasound imaging device and a method of generating an ultrasound image. The ultrasound image generation method may include steps of
(Continued)

transmitting an ultrasound signal to an object, receiving an ultrasound echo signal from the object, generating ultrasound image data on the basis of the received ultrasound echo signal, identifying a fetus's skull and an anatomical structure of a mother's body from the ultrasound image data, identifying a progression direction of the fetus's skull on the basis of a correspondence relationship between the fetus's skull and the anatomical structure of the mother's body, and displaying information on the progression direction of the fetus's skull.

15 Claims, 13 Drawing Sheets

(58) Field of Classification Search
CPC ....... A61B 8/4472; A61B 8/463; A61B 8/464; A61B 8/483; A61B 8/5223; G16H 30/40; G16H 50/30
See application file for complete search history.

(56) References Cited

U.S. PATENT DOCUMENTS

| | | | |
|---|---|---|---|
| 8,848,994 | B2 | 9/2014 | Lee et al. |
| 9,603,579 | B2 | 3/2017 | Lee et al. |
| 9,947,097 | B2 | 4/2018 | Perrey et al. |
| 10,368,833 | B2 | 8/2019 | Patruno et al. |
| 2006/0015036 | A1 | 1/2006 | Paltieli |
| 2009/0093716 | A1* | 4/2009 | Deischinger ......... A61B 8/0866 600/443 |
| 2014/0296711 | A1 | 10/2014 | Lee |
| 2016/0045152 | A1 | 2/2016 | Singhal et al. |
| 2016/0074006 | A1* | 3/2016 | Patruno ............... A61B 8/5223 600/443 |
| 2018/0161010 | A1* | 6/2018 | Choi ...................... A61B 8/54 |
| 2018/0185003 | A1 | 7/2018 | Zou et al. |
| 2019/0012432 | A1* | 1/2019 | Sokulin ................ G06T 7/0012 |

FOREIGN PATENT DOCUMENTS

| | | | |
|---|---|---|---|
| JP | 2006-167100 | A | 6/2006 |
| JP | 2009-90107 | A | 4/2009 |
| JP | 2011-183147 | A | 9/2011 |
| JP | 5400343 | B2 | 11/2013 |
| JP | 2014-124269 | A | 7/2014 |
| JP | 2015-171476 | A | 10/2015 |
| JP | 2018-068687 | A | 5/2018 |
| JP | 6417363 | B2 | 10/2018 |
| KR | 10-2011-0061291 | A | 6/2011 |
| KR | 10-2011-0064101 | A | 6/2011 |
| KR | 10-2013-0082318 | A | 7/2013 |
| KR | 10-2014-0118058 | A | 10/2014 |
| KR | 10-2017-0053685 | A | 5/2017 |
| WO | 2017/194392 | A1 | 11/2017 |

OTHER PUBLICATIONS

Ghi T. et al., "Diagnosis of station and rotation of the fetal head in the second stage of labor with intrapartum translabial ultrasound," Ultrasound in Obstetrics and Gynecology, vol. 33, No. 3, Mar. 1, 2009, pp. 331-336.
Ghi T. et al., "Three-dimensional ultrasound in monitoring progression of labor: a reproducibility study," Ultrasound in Obstetrics and Gynecology, vol. 36, No. 4, Jul. 22, 2010, pp. 500-506.
International Written Opinion and Search Report dated Oct. 30, 2019 issued in International Patent Application No. PCT/KR2019/005836 (English translation).
T. Ghi et al., "ISUOG Practice Guidelines: intrapartum ultrasound," Ultrasound Obstet Gynecol, 2018, 52, pp. 128-139.
W. Henrich et al., "Intrapartum translabial ultrasound (ITU): sonographic landmarks and correlation with successful vacuum extraction," Ultrasound Obstet Gynecol, 2006, 28, pp. 753-760.
Korean Office Action dated Sep. 11, 2023 issued in Korean Patent Application No. 10-2019-0011984 (along with English translation).
Korean Notice of Allowance dated May 27, 2024 issued in Korean Patent Application No. 10-2019-0011984 (with English translation).
Office Action dated Jan. 10, 2025, issued in corresponding European Patent Application No. 19912750.7.

* cited by examiner

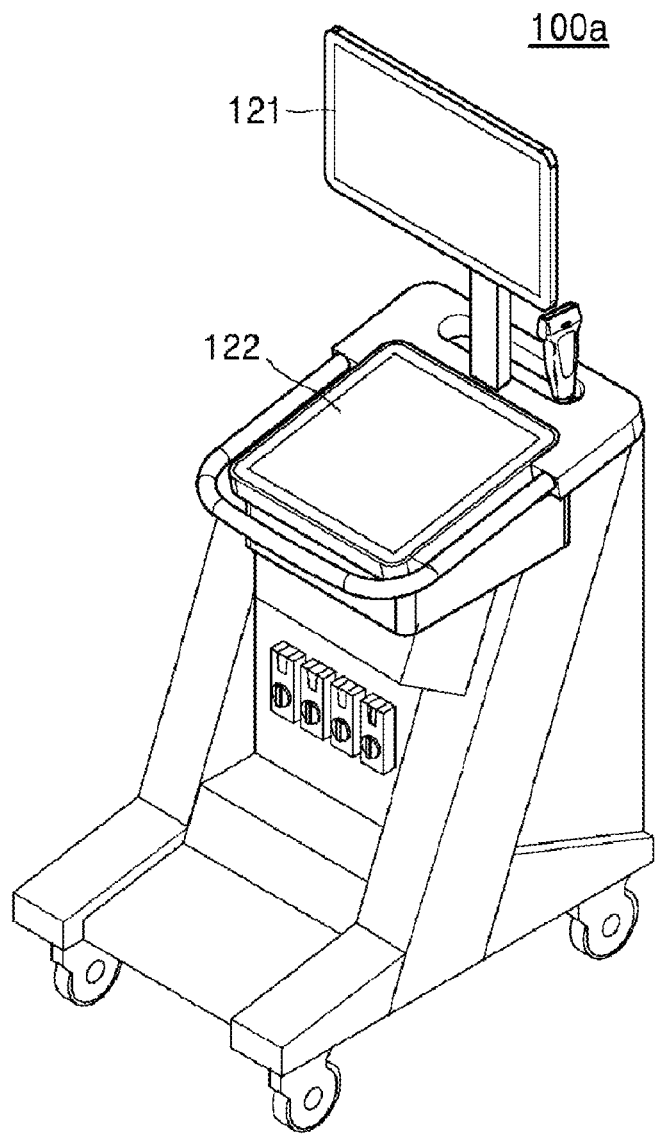

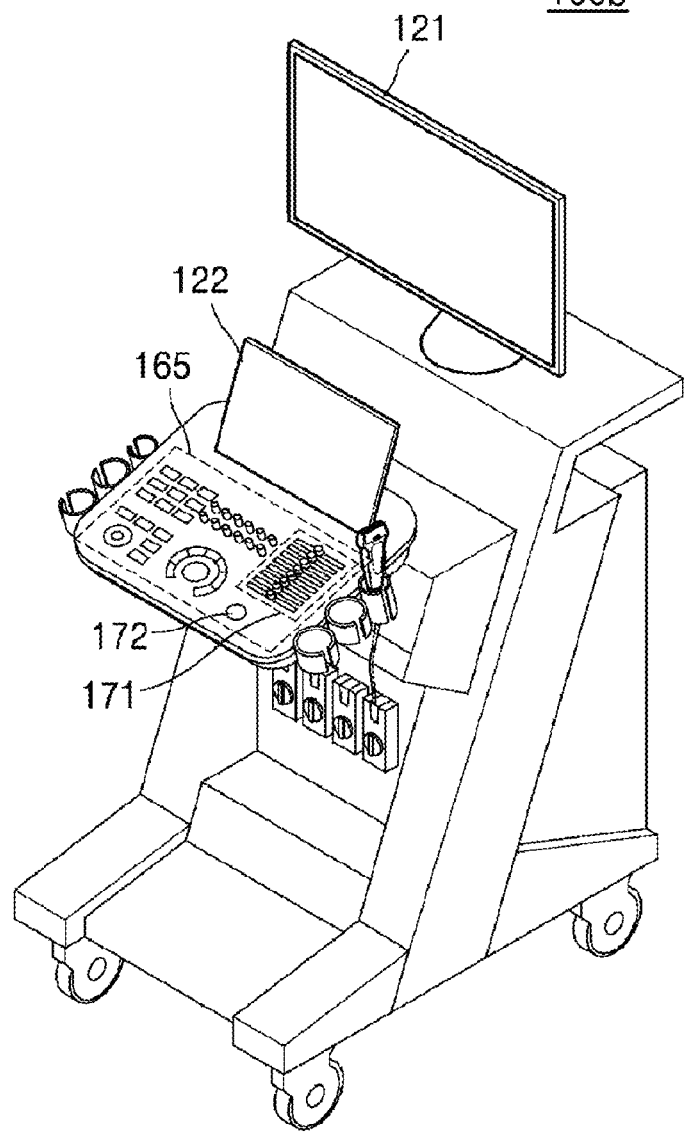

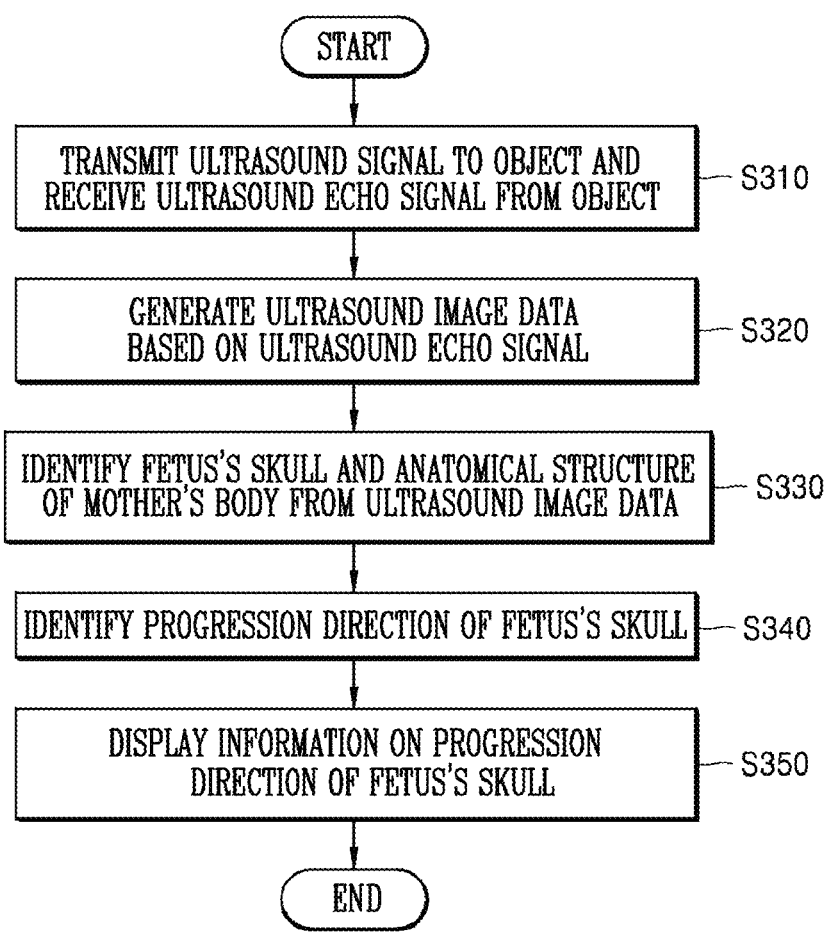

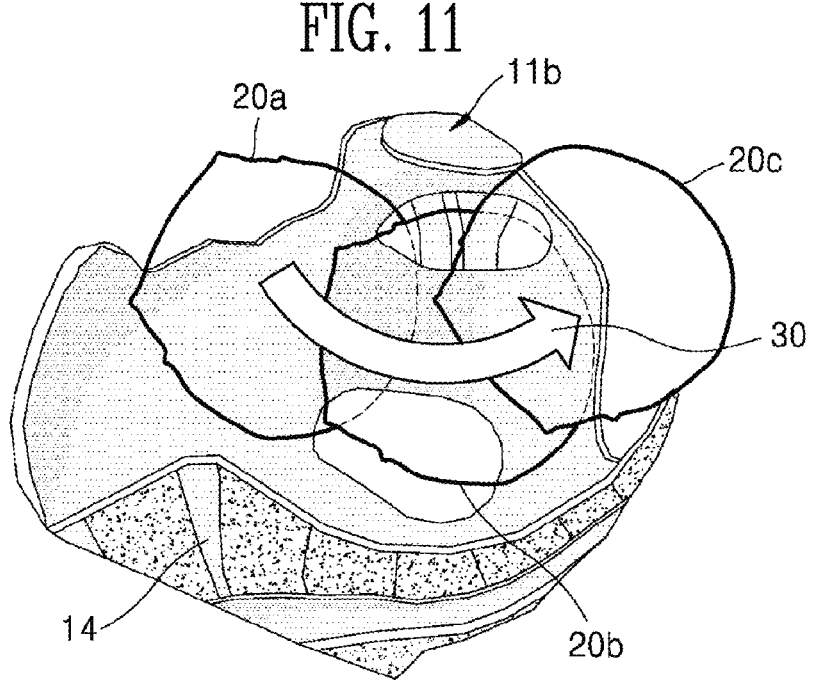

ULTRASOUND IMAGING DEVICE AND ULTRASOUND IMAGE GENERATION METHOD FOR IDENTIFYING DEGREE OF DELIVERY PROGRESS OF FETUS

CROSS-REFERENCE OF RELATED APPLICATIONS

This application is the U.S. National Phase under 35 U.S.C. § 371 of International Patent Application No. PCT/KR2019/005836, filed on May 15, 2019, which in turn claims the benefit of Korean Application No. 10-2019-0011984, filed on Jan. 30, 2019, the entire disclosures of which applications are incorporated by reference herein.

TECHNICAL FIELD

Disclosed embodiments relate to an ultrasound imaging device and a method of generating an ultrasound image using the same.

BACKGROUND ART

An ultrasound imaging device irradiates ultrasound signals generated from transducers of a probe to an object and receives information on signals reflected from the object, thereby obtaining at least one image of an internal part of the object (e.g., soft tissue or blood flow).

The ultrasound imaging device has advantages of being compact and inexpensive, and displaying images in real time. Further, as the ultrasound imaging device is very safe due to lack of radiation exposure, the ultrasound imaging device is widely used together with other imaging diagnosis apparatuses such as an X-ray diagnosis device, a computed tomography (CT) scanner, a magnetic resonance imaging (MRI) device, a nuclear medicine diagnosis apparatus, and the like.

The ultrasound imaging device is used to check the status of a fetus, such as a size, growth rate, and normal development of the fetus from an early stage of mother's pregnancy until delivery of the fetus. Further, the ultrasound imaging device is used to check fetal conditions and the position of a skull of the fetus.

FIG. 10 is a diagram illustrating a structure of a pelvis of a mother's body. Referring to FIG. 10, the pelvis of the mother's body is composed of a sacrum 14, an ilium 13, an ischium 12, a pubis 11a, and a cartilage plate 11b of pubic symphysis. A fetus that is grown in the mother's body passes through the pelvis to be delivered.

FIG. 11 is a view illustrating a progression direction of a skull of the fetus when the fetus is delivered. Referring to FIG. 11, the fetus passes between the sacrum 14 and the cartilage plate 11b of pubic symphysis of the mother's body. A skull 20a, 20b, or 20c of the fetus rotates with respect to the cartilage plate 11b of pubic symphysis while moving along the sacrum 14.

When the skull 20a, 20b, or 20c of the fetus moves along a moving path 30, the progression direction of the skull 20a, 20b, or 20c of the fetus is changed. Specifically, the skull 20a of the fetus in a first period moves downward with respect to the cartilage plate 11b of pubic symphysis. The skull 20b of the fetus in a second period moves in a horizontal direction with respect to the cartilage plate 11b of pubic symphysis. The skull 20c of the fetus in a third period moves upward with respect to the cartilage plate 11b of pubic symphysis. Thus, on the basis of the progression direction of the skull 20a, 20b, or 20c of the fetus, a degree of fetal delivery progress may be identified. That is, on the basis of the results of identifying the progression direction of the skull 20a, 20b, or 20c of the fetus, the fetal delivery be prepared.

Accordingly, there is a need for an ultrasound imaging device capable of easily identifying a progression direction of a fetus's skull in a mother's body so that fetal delivery may be prepared smoothly.

DISCLOSURE

Technical Problem

Disclosed embodiments are directed to an ultrasound imaging device and a method of generating an ultrasound image, capable of identifying a direction of a fetus's skull.

Technical Solution

As a technical means for achieving the above-described technical problem, a method of generating an ultrasound image by an ultrasound imaging device according to a first aspect of the present disclosure, may include steps of transmitting an ultrasound signal to an object, receiving an ultrasound echo signal from the object, generating ultrasound image data on the basis of the received ultrasound echo signal, identifying a fetus's skull and an anatomical structure of a mother's body from the ultrasound image data, identifying a progression direction of the fetus's skull on the basis of a correspondence relationship between the fetus's skull and the anatomical structure of the mother's body, and displaying information on the progression direction of the fetus's skull.

The anatomical structure of the mother's body may be a cartilage plate of pubis symphysis of the mother's body, and the step of identifying the progression direction of the fetus's skull may include a step of identifying the progression direction of the skull on the basis of an angle between the cartilage plate of pubis symphysis of the mother's body and the skull.

The step of identifying the fetus's skull and the anatomical structure of the mother's body from the ultrasound image data may include steps of identifying a major axis of the cartilage plate of pubis symphysis of the mother's body, identifying an ellipse corresponding to the fetus's skull, and identifying a major axis of the ellipse, and the step of identifying the progression direction of the fetus's skull may include a step of identifying the progression direction of the skull on the basis of an angle between the major axis of the cartilage plate of pubis symphysis of the mother's body and the major axis of the ellipse.

The step of generating the ultrasound image data may include a step of generating a plurality of ultrasound cross-sectional images each including the fetus's skull and the anatomical structure of the mother's body, and the step of identifying the fetus's skull and the anatomical structure of the mother's body may include steps of identifying the major axis of the cartilage plate of pubis symphysis of the mother's body from each of the plurality of ultrasound cross-sectional images, selecting the ultrasound cross-sectional image having the cartilage plate of pubis symphysis of the mother's body whose major axis is the longest from among the plurality of ultrasound cross-sectional images, and identifying an ellipse corresponding to the fetus's skull and a major axis of the ellipse from the selected cross-sectional image.

The method may further include a step of displaying a marker indicating the major axis of the cartilage plate of pubic symphysis and a marker indicating the major axis of the ellipse.

The method may further include a step of rotating the ultrasound image such that the major axis of the cartilage plate of pubic symphysis is in a horizontal state, and displaying the rotated ultrasound image.

The method may further include steps of identifying a degree of fetal delivery progress on the basis of the angle between the major axis of the cartilage plate of pubis symphysis of the mother's body and the major axis of the ellipse, and displaying information on the degree of fetal delivery progress.

The step of displaying the information on the degree of fetal delivery progress may include a step of displaying a virtual fetal model corresponding to the degree of fetal delivery progress.

The step of identifying the fetus's skull and the anatomical structure of the mother's body from the ultrasound image data may include steps of receiving a user input for selecting at least one of the cartilage plate of pubic symphysis and the fetus's skull from a user and, identifying at least one of a region corresponding to the cartilage plate of pubic symphysis and a region corresponding to the fetus's skull on the basis of the user input.

As a technical means for achieving the above-described technical problem, an ultrasound imaging device according to a second aspect of the present disclosure may include an ultrasound probe configured to transmit an ultrasound signal to an object and receive an ultrasound echo signal from the object, a processor configured to generate ultrasound image data on the basis of the received ultrasound echo signal, identify a fetus's skull and an anatomical structure of a mother's body from the ultrasound image data, and identify a progression direction of the fetus's skull on the basis of a correspondence relationship between the fetus's skull and the anatomical structure of the mother's body, and a display unit configured to display information on the progression direction of the fetus's skull.

The anatomical structure of the mother's body may be a cartilage plate of pubis symphysis of the mother's body, and the processor may identify the progression direction of the skull on the basis of an angle between the cartilage plate of pubis symphysis of the mother's body and the skull.

The processor may identify a major axis of the cartilage plate of pubis symphysis of the mother's body, identify an ellipse corresponding to the fetus's skull, identify a major axis of the ellipse, and identify the progression direction of the skull on the basis of an angle between the major axis of the cartilage plate of pubis symphysis of the mother's body and the major axis of the ellipse.

The processor may generate a plurality of ultrasound cross-sectional images each including the fetus's skull and the anatomical structure of the mother's body, identify a major axis of the cartilage plate of pubis symphysis of the mother's body from each of the plurality of ultrasound cross-sectional images, select the ultrasound cross-sectional image having the cartilage plate of pubis symphysis of the mother's body whose major axis is the longest from among the plurality of ultrasound cross-sectional images, and identify an ellipse corresponding to the fetus's skull and a major axis of the ellipse from the selected cross-sectional image.

The display unit may display a marker indicating the major axis of the cartilage plate of pubic symphysis and a marker indicating the major axis of the ellipse.

The display unit may rotate the ultrasound image such that the major axis of the cartilage plate of pubic symphysis is in a horizontal state, and display the rotated ultrasound image.

The processor may identify a degree of fetal delivery progress on the basis of the angle between the major axis of the cartilage plate of pubis symphysis of the mother's body and the major axis of the ellipse, and the display unit may display information on the degree of fetal delivery progress.

The display unit may display a virtual fetal model corresponding to the degree of fetal delivery progress.

The ultrasound imaging device may further include an input unit configured to receive a user input for selecting at least one of the cartilage plate of pubic symphysis and the fetus's skull from a user, and the processor may identify at least one of a region corresponding to the cartilage plate of pubic symphysis and a region corresponding to the fetus's skull on the basis of the user input.

As a technical means for achieving the above-described technical problem, according to a third aspect of the present disclosure, there are provided a computer-readable recording medium in which instructions that may be executed in a computer are recorded and a computer program product including the recording medium, wherein the recording medium may be a medium in which the instructions enabling the ultrasound imaging device to execute the ultrasound image generation method according to the first aspect of the present disclosure are recorded.

DESCRIPTION OF DRAWINGS

FIG. 2A is a view illustrating ultrasound imaging devices according to an embodiment.

FIG. 2B is a view illustrating ultrasound imaging devices according to an embodiment.

FIG. 3 is a flowchart illustrating a method of generating an ultrasound image by an ultrasound imaging device, according to an embodiment.

FIG. 11 is a view illustrating a progression direction of a fetus's skull when the fetus is delivered.

MODES OF THE INVENTION

Figure 1:
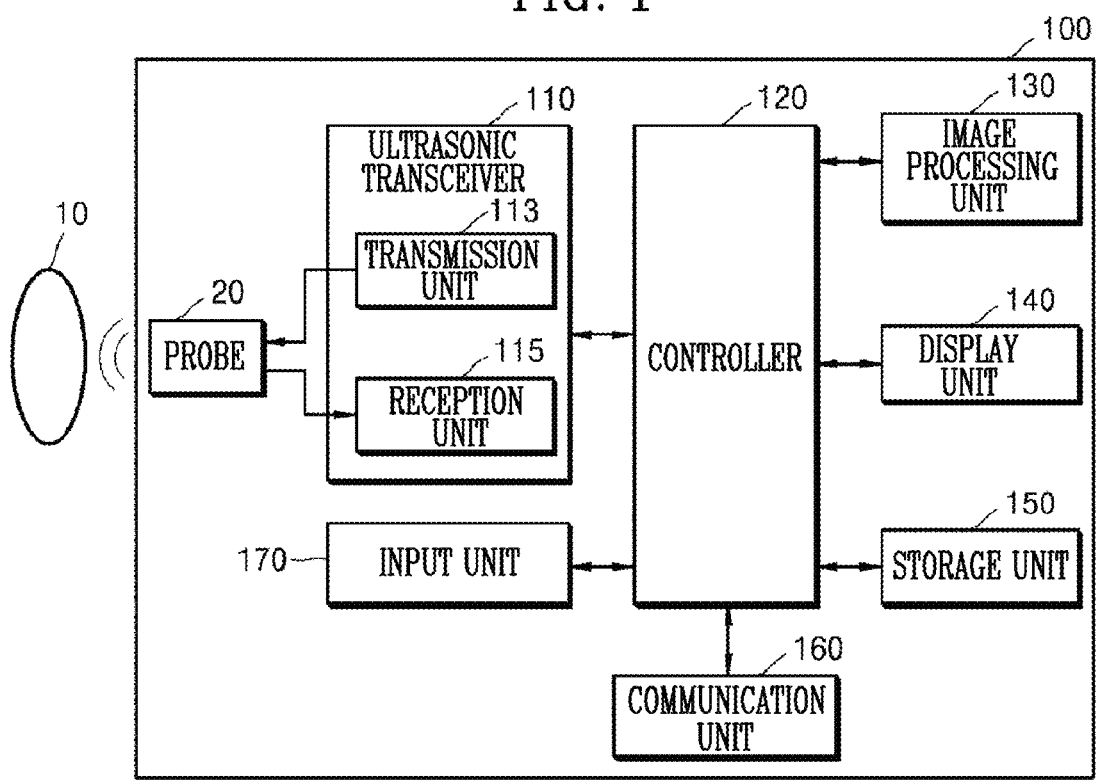
FIG. 1 is a block diagram illustrating a configuration of an ultrasound imaging device according to an embodiment.

The present specification describes the principles of the present invention and discloses embodiments such that the scope of the present invention may be clarified and those skilled in the art to which the present invention pertains may implement the present invention. The disclosed embodiments may be implemented in various forms.

Throughout the specification, like reference numerals refer to like elements. This specification does not describe all components of embodiments, and common descriptions in the technical field to which the present disclosure pertains and redundant descriptions between the embodiments will be omitted. Terms such as "part" and "portion" used herein may be implemented as software or hardware. According to embodiments, a plurality of parts or portions may be implemented as a single unit or element, or a single part or portion may include a plurality of elements. Hereinafter, an operation principle and the embodiments of the present disclosure will be described with reference to the accompanying drawings.

In the present specification, an "image" may include a medical image obtained by a medical imaging apparatus such as a magnetic resonance imaging (MRI) device, a computed tomography (CT) device, an ultrasound imaging device, and an X-ray imaging device.

In the present specification, an "object" is to be photographed and may include a person, an animal, or a part thereof. For example, the object may include a part (organ) of a human body, a phantom, or the like. As another example, the subject may include at least a part of a mother's body having a fetus therein.

Throughout the specification, an "ultrasonic image" means an image of the object, which is processed based on an ultrasonic signal transmitted to the object and reflected from the object.

Hereinafter, the embodiments will be described in detail with reference to the accompanying drawings.

FIG. 1 is a block diagram illustrating a configuration of an ultrasound imaging device 100 according to an embodiment. The ultrasound imaging device 100 may include a probe 20, an ultrasonic transceiver 110, a controller 120, an image processing unit 130, a display unit 140, a storage unit 150, a communication unit 160, and an input unit 170.

The ultrasound imaging device 100 may be implemented as a portable type as well as a cart type. Examples of a portable ultrasound imaging device may include a smart phone, a laptop computer, a personal digital assistant (PDA), a tablet personal computer (PC), and the like including a probe and an application, but the present invention is not limited thereto.

The probe 20 may include a plurality of transducers. The plurality of transducers may transmit ultrasonic signals to an object 10 according to a transmission signal applied from a transmission unit 113. The plurality of transducers may receive ultrasonic signals reflected from the object 10 to form a reception signal. Further, the probe 20 may be implemented integrally with the ultrasound imaging device 100 or may be implemented as a separate type in which the probe 20 is connected to the ultrasound imaging device 100 in a wired or wireless manner. Further, the ultrasound imaging device 100 may include one or more probes 20 according to an implementation form.

The controller 120 controls the transmission unit 113 to form a transmission signal to be applied to each of the plurality of transducers in consideration of the positions and focal points of the plurality of transducers included in the probe 20.

The controller 120 controls a reception unit 115 to convert a reception signal received from the probe 20 in an analog-to-digital conversion manner and to sum the digitally converted reception signal in consideration of the positions and focal points of the plurality of transducers, thereby generating ultrasonic data. The controller 120 may include the image processing unit 130.

The image processing unit 130 generates an ultrasonic image using the ultrasonic data generated by the ultrasonic reception unit 115.

The display unit 140 may display the generated ultrasonic image and various pieces of information processed by the ultrasound imaging device 100. The ultrasound imaging device 100 may include one or more display units 140 according to an implementation form. Further, the display unit 140 may be implemented as a touch screen in combination with a touch panel.

The controller 120 may control the overall operation of the ultrasound imaging device 100 and a signal flow between internal components of the ultrasound imaging device 100. The controller 120 may include a memory that stores a program or data for performing a function of the ultrasound imaging device 100 and a processor that processes the program or data. The processor may perform functions for performing the disclosed embodiments with reference to FIGS. 3 to 9, and may control components of the ultrasound imaging device 100. The processor may include a general-purpose processor (e.g., a central processing unit (CPU)) or a special-purpose processor manufactured for generating an ultrasound image.

At least one processor may operate as the image processing unit 130. That is, the processor may generate an ultrasound image using ultrasound data.

Further, the processor may identify a predetermined region in the ultrasound image and measure at least one of a thickness, an area, and a volume of the predetermined region.

Further, the processor may also obtain additional information on the predetermined region. The processor may execute an instruction or application for obtaining additional information that is used to facilitate a diagnosis by a user.

Further, the controller 120 may control the operation of the ultrasonic imaging device 100 by receiving a control signal from the input unit 170 or an external device.

The ultrasound imaging device 100 may include the communication unit 160 and may be connected, through the communication unit 160, to an external device (for example, a server, a medical device, a portable device (a smart phone, a tablet PC, a wearable device, and the like)).

The communication unit 160 may include one or more components enabling communication with the external device and may include, for example, at least one of a short-range communication module, a wired communication module, and a wireless communication module.

The communication unit 160 may receive a control signal and data from the external device and transmit the received control signal to the controller 120 so that the controller 120 may control the ultrasound imaging device 100 in response to the received control signal.

Alternatively, the controller 120 may transmit a control signal to the external device through the communication unit 160 so that the external device may be controlled in response to the control signal of the controller 120.

For example, the external device may process the data of the external device in response to the control signal of the controller received through the communication unit.

A program capable of controlling the ultrasound imaging device 100 may be installed in the external device, and the program may include instructions for performing some or all of the operations of the controller 120.

The program may be installed in the external device in advance or may be installed by a user of the external device by downloading the program from a server that provides applications. The server that provides applications may include a recording medium in which the corresponding program is stored.

The storage unit 150 may store various types of data or programs for driving and controlling the ultrasound imaging device 100, input/output ultrasonic data, acquired ultrasonic images, and the like. The storage unit 150 may include a transitory memory (e.g., a random access memory (RAM), a buffer, and the like) or a non-transitory memory (e.g., a data storage such as a magnetic disc).

The input unit 170 may receive a user's input to control the ultrasound imaging device 100. For example, the user's input may include an input for manipulating a button, a keypad, a mouse, a trackball, a jog switch, a knob, or the like, an input for touching a touchpad or a touch screen, a voice input, a motion input, and a bioinformation input (e.g., iris recognition or fingerprint recognition), but the present disclosure is not limited thereto.

An example of the ultrasound imaging device 100 according to an embodiment will be described below with reference to FIGS. 2A to 2C.

Figure 2C:
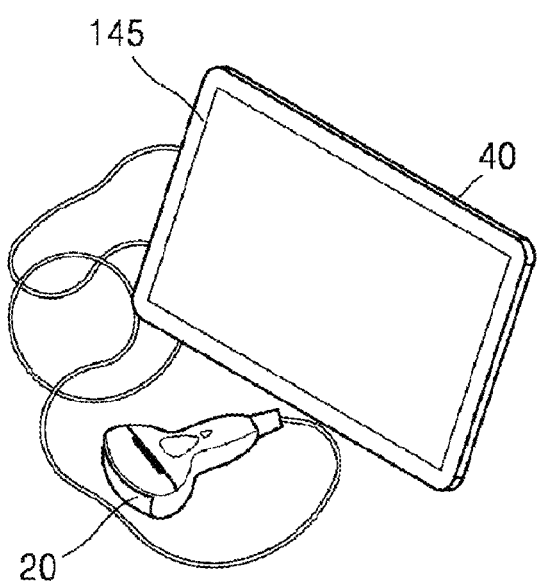
FIG. 2C is a view illustrating ultrasound imaging devices according to an embodiment.

FIGS. 2A to 2C are views illustrating ultrasound imaging devices according to an embodiment.

Referring to FIGS. 2A and 2B, ultrasound imaging devices 100a and 100b may each include a main display unit 121 and a sub display unit 122. One of the main display unit 121 and the sub display unit 122 may be implemented as a touch screen. The main display unit 121 and the sub display unit 122 may display the ultrasonic image or various pieces of information processed by the ultrasound imaging devices 100a and 100b. Further, the main display unit 121 and the sub display unit 122 may be implemented as a touch screen and provide a graphical user interface (GUI) to receive data for controlling the ultrasound imaging devices 100a and 100b from a user. For example, the main display unit 121 may display the ultrasonic image, and the sub display unit 122 may display a control panel for controlling the ultrasonic image in the form of the GUI. The sub display unit 122 may receive data for controlling the displaying of the image through the control panel displayed in the form of the GUI. The ultrasound imaging devices 100a and 100b may control, using input control data, the displaying of the ultrasonic image displayed on the main display unit 121.

Referring to FIG. 2B, the ultrasound imaging device 100b may further include a control panel 165 in addition to the main display unit 121 and the sub display unit 122. The control panel 165 may include a button, a trackball, a jog switch, a knob, and the like, and may receive data for controlling the ultrasound imaging device 100b from the user. For example, the control panel 165 may include a time gain compensation (TGC) button 171, a freeze button 172, and the like. The TGC button 171 is a button for setting a TGC value for each depth of the ultrasonic image. Further, when detecting the input of the freeze button 172 while scanning the ultrasonic image, the ultrasound imaging device 100b may maintain a state in which a frame image at a corresponding time point is displayed.

Meanwhile, inputs of the button, the trackball, the jog switch, the knob, and the like included in the control panel 165 may be provided to the GUI in the main display unit 121 or the sub display unit 122.

Referring to FIG. 2C, the ultrasound imaging device 100c may be implemented as a portable type. Examples of a portable ultrasound imaging device 100c may include a smart phone, a laptop computer, a PDA, a tablet PC, and the like including a probe and an application, but the present invention is not limited thereto.

The ultrasound imaging device 100c may include the probe 20 and a main body 40, and the probe 20 may be connected to one side of the main body 40 in a wired or wireless manner. The main body 40 may include a touch screen 145. The touch screen 145 may display the ultrasonic image, various pieces of information processed by the ultrasound imaging device, the GUI, and the like.

FIG. 3 is a flowchart illustrating a method of generating an ultrasound image by the ultrasound imaging device, according to an embodiment.

Referring to step S310, the ultrasound probe 20 of the ultrasound imaging device 100 may transmit an ultrasound signal to the object 10 and receive an ultrasound echo signal from the object 10. For example, the convex ultrasound probe 20 may transmit an ultrasound signal with frequencies of 3 to 5 MHz to the object 10. The ultrasound probe 20 may receive an ultrasound echo signal generated by reflecting the ultrasound signal from the object 10.

Referring to step S320, the processor of the ultrasound imaging device 100 may generate ultrasound image data on the basis of the received ultrasound echo signal.

According to an embodiment, the ultrasound image data may include at least one of data for generating a two-dimensional (2D) ultrasound image and data for generating a three-dimensional (3D) ultrasound image. Further, the ultrasound image data may include data for generating a plurality of ultrasound cross-sectional images.

According to an embodiment, the ultrasound image data may include image data related to a fetus's skull and at least one anatomical structure of the mother's body (e.g., a cartilage plate of pubic symphysis).

Referring to step S330, the processor of the ultrasound imaging device 100 may identify, from the ultrasound image data, the fetus's skull and the anatomical structure of the mother's body (e.g., the cartilage plate of pubic symphysis).

According to an embodiment, the processor may identify the fetus's skull and the anatomical structure of the mother's body (e.g., a cross section of the cartilage plate of pubic symphysis) from each of the plurality of ultrasound cross-sectional images.

According to an embodiment, the processor may identify at least one of the fetus's skull and the anatomical structure of the mother's body on the basis of a user input received through an input unit 170 such as a touch screen, a touchpad, a keyboard, a mouse, a trackball, and a jog switch.

According to an embodiment, the processor may identify at least one of the fetus's skull and the anatomical structure of the mother's body by comparing a predetermined shape identified from the ultrasound image data with a previously stored outer shape. For example, the processor may identify a cross section of the cartilage plate (disc) of pubic symphysis of the mother's body by comparing the predetermined shape identified from the ultrasound image data with the previously stored anatomical structure model. As another example, the processor may identify the fetus's skull by identifying a region that is composed of pixels having high brightness values in the ultrasound image data and includes at least a portion having an elliptical shape. As still another example, the processor may identify a pubis of the mother's body, and pixels with high brightness values positioned near the pubis. The processor may identify the skull from pixels that are positioned at a predetermined distance from the cartilage plate of pubic symphysis among the pixels having high brightness values and constitute the elliptical-shaped region.

The processor may identify the fetus's skull and the anatomical structure of the mother's body from the ultrasound image data using various algorithms disclosed in the related art.

Referring to step S340, the processor of the ultrasound imaging device 100 may identify a progression direction of the skull on the basis of the identified anatomical structure of the mother's body and skull.

According to an embodiment, the processor may identify the progression direction of the skull on the basis of an angle between the cartilage plate of pubic symphysis of the mother's body and the skull. For example, the processor may identify the progression direction of the skull on the basis of an angle between a major axis of the cartilage plate of pubic symphysis and a major axis of an ellipse corresponding to the skull. Details thereof will be described below with reference to FIG. 5.

According to an embodiment, the processor may identify the progression direction of the skull on the basis of a cross-sectional image having the longest major axis of the cartilage plate of pubic symphysis, from the plurality of ultrasound cross-sectional images. Details thereof will be described below with reference to FIG. 6.

Referring to step S350, the display unit 140 of the ultrasound imaging device 100 may display information on the progression direction of the fetus's skull.

The information on the progression direction of the fetus's skull may include information on an outer shape of the skull, information on a moving path of the skull, information on the angle between the major axis of the ellipse corresponding to the skull and the major axis of the cartilage plate of pubic symphysis of the mother's body, information on an outer shape of the cartilage plate of pubic symphysis, information on a degree of fetal delivery progress in the mother's body, and information on a virtual fetal model corresponding to the degree of delivery progress, but the present disclosure is not limited thereto.

According to an embodiment, the display unit 140 may display information on the outer shape of the skull. In addition, the display unit 140 may display information on the outer shape of the cartilage plate of pubic symphysis of the mother's body. Details thereof will be described below with reference to FIG. 4.

According to an embodiment, the display unit 140 may display information on the moving path of the fetus's skull. Details thereof will be described below with reference to FIG. 4.

According to an embodiment, the display unit 140 may display a marker related to the major axis of the ellipse corresponding to the skull and the major axis of the cartilage plate of pubic symphysis. In addition, the display unit 140 may display information on the angle between the major axis of the ellipse and the major axis of the cartilage plate of pubic symphysis. Details thereof will be described below with reference to FIG. 5.

According to an embodiment, the display unit 140 may rotate the ultrasound image such that the major axis of the cartilage plate of pubic symphysis is in a horizontal state and display the rotated image. Details thereof will be described below with reference to FIG. 7.

According to an embodiment, the display unit 140 may display information on the degree of fetal delivery progress in the mother's body. For example, the display unit 140 may color-code a partial region of the ultrasound image with a color corresponding to the degree of fetal delivery progress and display the color-coded region. Specifically, the processor may identify the degree of fetal delivery progress in the mother's body on the basis of the angle between the major axis of the cartilage plate of pubic symphysis and the major axis of the ellipse corresponding to the fetus's skull. The processor may color-code an inside of the ellipse with a color corresponding to the degree of fetal delivery progress. The display unit 140 may display the color-coded ellipse. Details thereof will be described below with reference to FIG. 8.

According to an embodiment, the display unit 140 may display the virtual fetal model corresponding to the degree of fetal delivery progress. The processor may identify the degree of fetal delivery progress in the mother's body on the basis of the angle between the major axis of the cartilage plate of pubic symphysis and the major axis of the ellipse corresponding to the fetus's skull. The processor may select the virtual fetal model image corresponding to the degree of fetal delivery progress from among the virtual fetal models previously stored in the storage unit 150. The display unit 140 may display the selected fetal model. Details thereof will be described below with reference to FIG. 9.

According to the disclosed embodiment, the user may easily recognize the progression direction of the fetus's skull. Thus, the user may easily recognize the degree of fetal delivery progress in the mother's body on the basis of the progression direction of the skull. That is, the ultrasound imaging device 100 may help the user such that the parturient woman safely delivers the fetus by displaying information on the progression direction of the skull.

Figure 4:
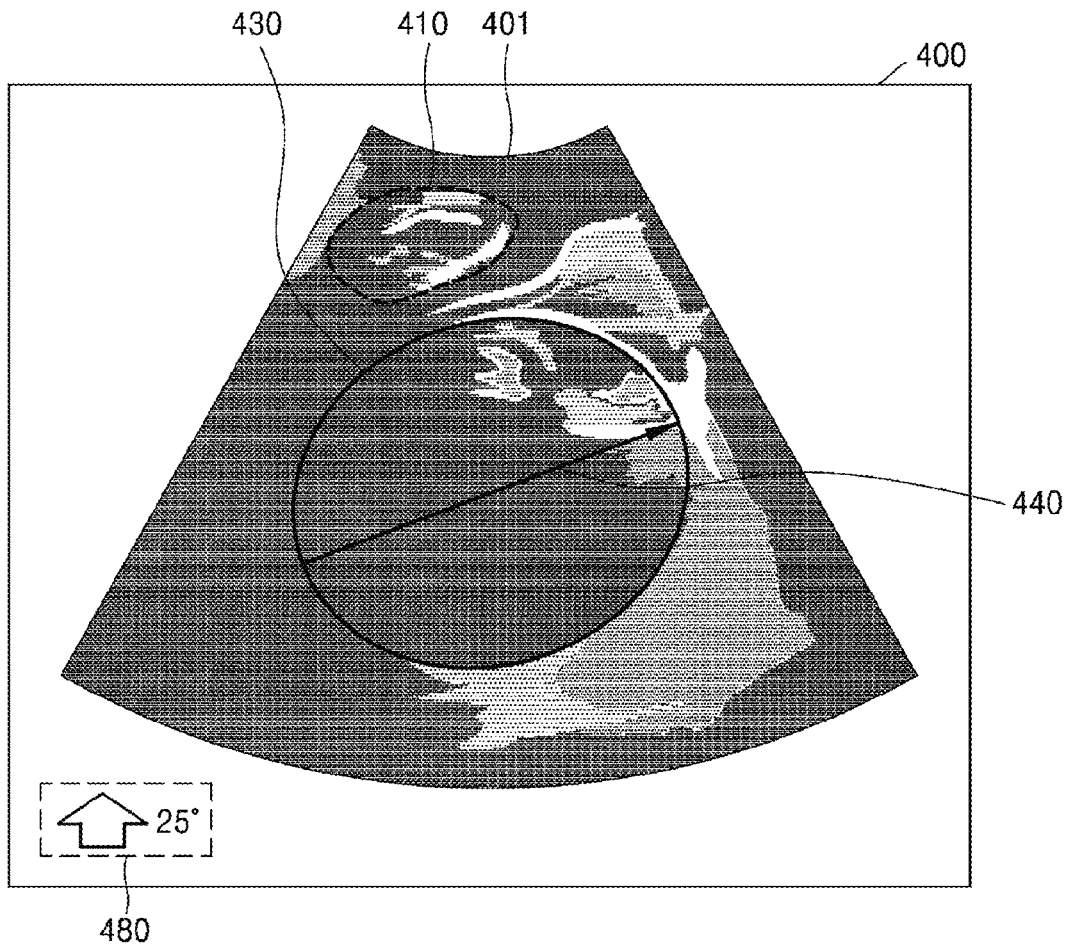
FIG. 4 is a view illustrating a case in which an ultrasound imaging device displays information on a progression direction of a fetus's skull, according to an embodiment.

FIG. 4 is a view illustrating a case in which an ultrasound imaging device displays information on a progression direction of a fetus's skull, according to an embodiment.

Referring to FIG. 4, an ultrasound imaging device 400 may display an ultrasound image 401 and information on a progression direction of a fetus's skull.

The ultrasound image 401 may include at least a portion of a fetus's skull 430 and at least one anatomical structure of the mother's body. The anatomical structure of the mother's body may include a cartilage plate 410 of pubic symphysis. The ultrasound imaging device 400 may identify the fetus's skull 430 and the cartilage plate 410 of pubic symphysis from the ultrasound image 401.

The cartilage plate 410 of pubic symphysis is positioned at a predetermined location even when the fetus's skull moves according to a degree of fetal delivery progress. A user may identify the progression direction of the fetus's skull on the basis of a correspondence relationship between the cartilage plate 410 of pubic symphysis and the fetus's skull 430. Accordingly, the ultrasound imaging device 400 may help the user to easily identify the progression direction of the fetus's skull by displaying information on the correspondence relationship between the cartilage plate 410 of pubic symphysis and the skull 430.

The ultrasound imaging device 400 may display information on an outer shape of the cartilage plate 410 of pubic symphysis. The outer shape of the cartilage plate of pubic symphysis may include an outer shape of a cross section of the cartilage plate of pubic symphysis. For example, the ultrasound imaging device 400 may represent an outline of the cartilage plate 410 of pubic symphysis with a line. That is, the ultrasound imaging device 400 may overlay a line of a predetermined color (e.g., white, yellow, or red) onto the outline of the cartilage plate 410 of pubic symphysis. As another example, the ultrasound imaging device 400 may color-code a region corresponding to the cartilage plate 410 of pubic symphysis with a predetermined color (e.g., green, yellow, blue, or red) and display the color-coded region.

The ultrasound imaging device 400 may display information on an outer shape of the skull 430. For example, the ultrasound imaging device 400 may represent an outline of the skull 430 with a line. That is, the ultrasound imaging device 400 may overlay a line of a predetermined color (e.g., white, yellow, or red) onto the outline of the skull 430. As another example, the ultrasound imaging device 400 may color-code a region corresponding the skull with a predetermined color (e.g., green, yellow, blue, or red) and display the color-coded region.

The ultrasound imaging device 400 may display information on the progression direction of the skull 430.

According to an embodiment, the ultrasound imaging device 400 may display information on the progression direction of the skull 430 with a marker 440 such as an arrow. For example, the ultrasound imaging device 400 may display information on the progression direction of the skull 430 by displaying a major axis of an ellipse corresponding to the fetus's skull 430 with an arrow.

According to an embodiment, the ultrasound imaging device 400 may display information on the progression direction of the skull 430 by displaying information 480 on an angle between the major axis of the ellipse corresponding to the skull 430 and a major axis of the cartilage plate 410 of pubic symphysis.

According to an embodiment, the ultrasound imaging device 400 may display information on the progression direction of the skull 430 by color-coding an inside of the ellipse corresponding to the skull with a color corresponding to the angle.

According to an embodiment, the ultrasound imaging device 400 may display information on a moving path of the skull 430 by overlaying a position of the skull onto the ultrasound image 401 every preset time unit.

Figure 5:
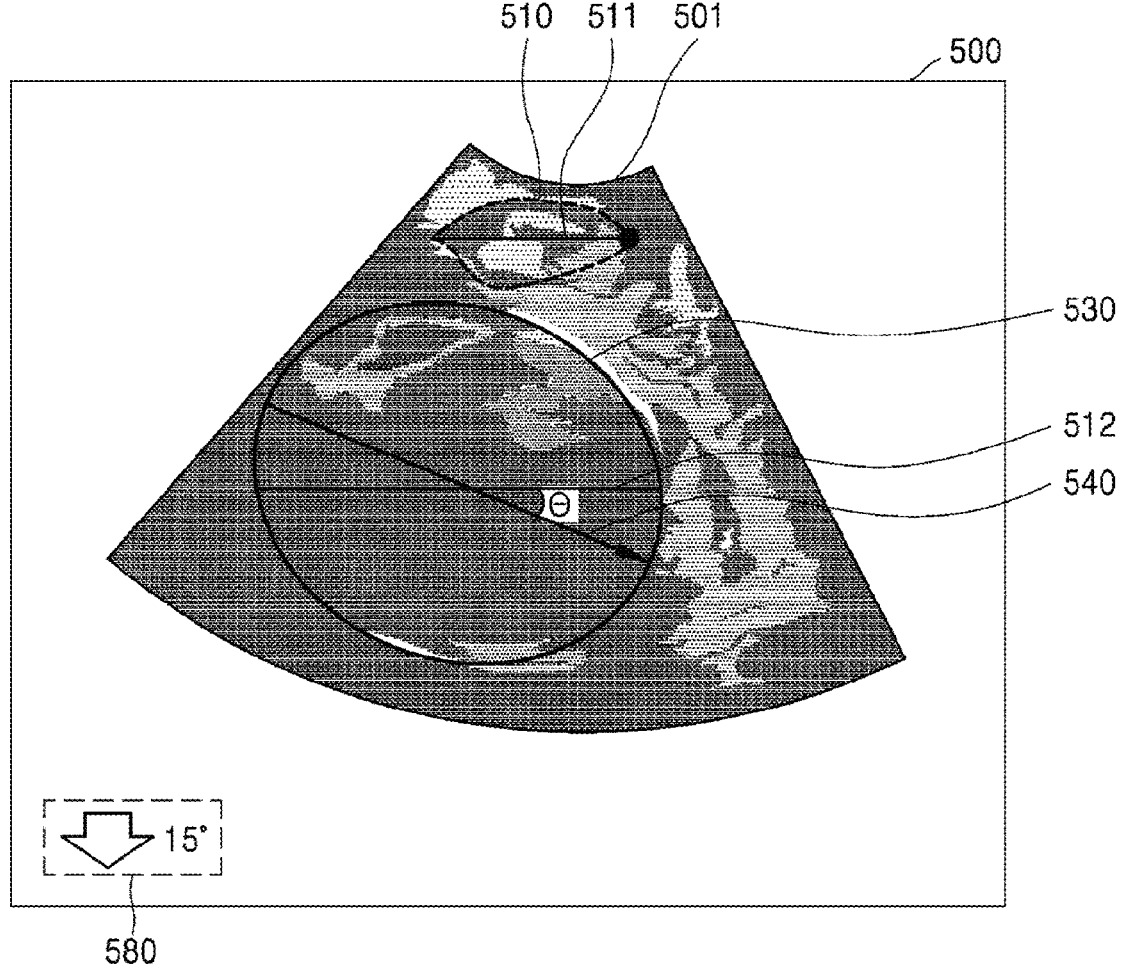
FIG. 5 is a view illustrating a case in which an ultrasound imaging device displays information on a progression direction of a fetus's skull, according to an embodiment.

FIG. 5 is a view illustrating a case in which an ultrasound imaging device displays information on a progression direction of a fetus's skull, according to an embodiment.

Referring to FIG. 5, an ultrasound imaging device 500 may identify a cartilage plate 510 of pubic symphysis of a mother's body and a fetus's skull 530 from an ultrasound image 501. The cartilage plate of pubic symphysis may include a cross section of the cartilage plate of pubic symphysis. The ultrasound imaging device 500 may identify a major axis 511 of the cartilage plate 510 of pubic symphysis and a major axis 540 of an ellipse corresponding to the skull 530.

According to an embodiment, the ultrasound imaging device 500 may measure an angle between the major axis 511 of the cartilage plate 510 of pubic symphysis and the major axis 540 of the ellipse corresponding to the skull 530. For example, the ultrasound imaging device 500 may generate a line 512 that is in contact with a portion of the major axis 540 of the ellipse and parallel to the major axis 511. The ultrasound imaging device 500 may measure the angle between the major axis 511 of the cartilage plate 510 of pubic symphysis and the major axis 540 of the ellipse corresponding to the skull 530 by measuring an angle between the line 512 and the major axis 540 of the ellipse.

The ultrasound imaging device 500 may help a user to easily identify the progression direction of the fetus's skull 530 by displaying the line 512, which is parallel to the major axis 511, together with the major axis 540 of the ellipse.

The ultrasound imaging device 500 may display information 580 on the angle between the major axis 511 of the cartilage plate 510 of pubic symphysis and the major axis 540 of the ellipse with at least one among symbols, letters, numerals, and colors. For example, the ultrasound imaging device 500 may represent the information 580 on the angle using symbols such as an arrow, or numerals.

Figure 6:
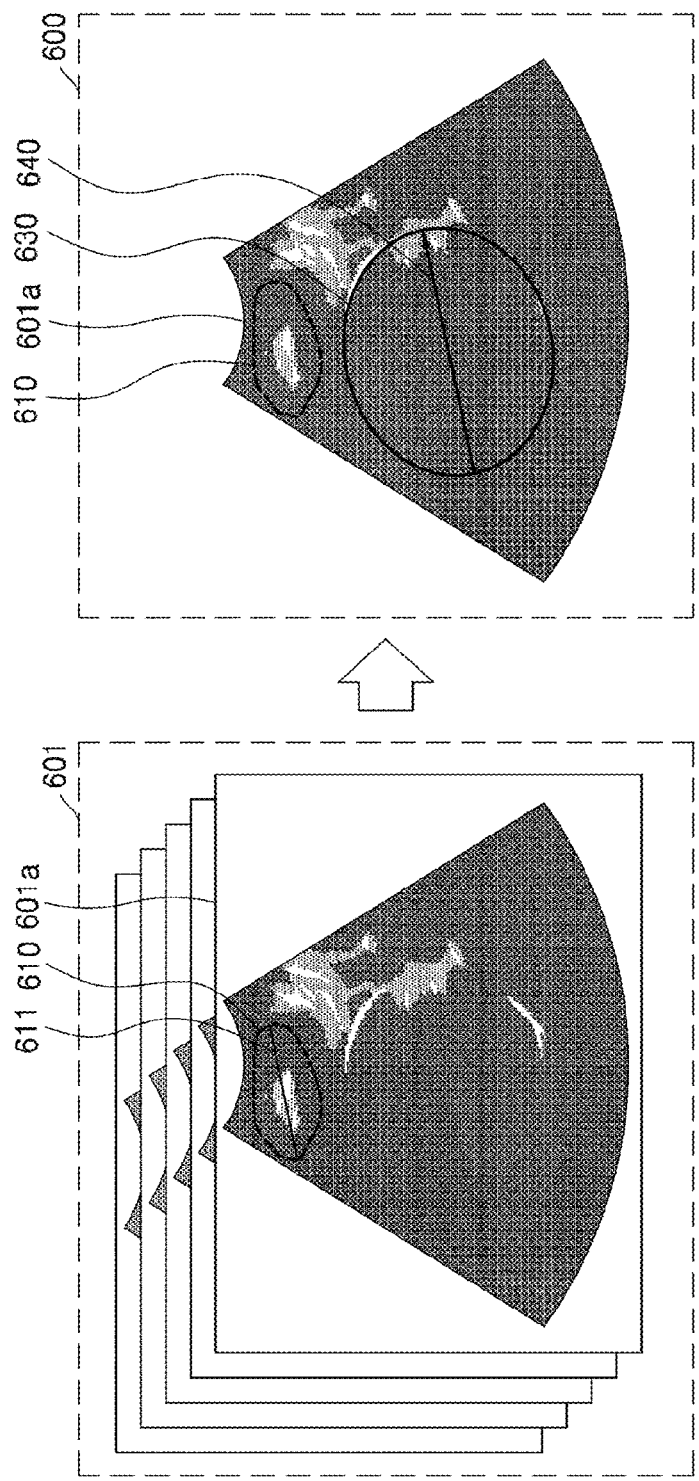
FIG. 6 is a view illustrating a case in which an ultrasound imaging device displays information on a progression direction of a fetus's skull from a plurality of ultrasound cross-sectional images, according to an embodiment.

FIG. 6 is a view illustrating a case in which an ultrasound imaging device displays information on a progression direction of a fetus's skull from a plurality of ultrasound cross-sectional images, according to an embodiment.

Referring to FIG. 6, an ultrasound imaging device 600 may obtain a plurality of ultrasound cross-sectional images 601.

According to an embodiment, the ultrasound imaging device 600 may select a reference cross-sectional image from among the plurality of ultrasound cross-sectional images 601 in order to identify the progression direction of the skull.

Specifically, the ultrasound imaging device 600 may identify a cross section of a cartilage plate of pubic symphysis from each of the plurality of ultrasound cross-sectional images 601. The ultrasound imaging device 600 may identify a major axis 611 of each of the identified cartilage plates of pubic symphysis. The ultrasound imaging device 600 may select an ultrasound image 601*a*, which has a cartilage plate 610 of pubic symphysis whose major axis 611 is the longest, as the reference cross-sectional image.

According to an embodiment, the ultrasound imaging device 600 may identify a skull 630 and a major axis 640 of an ellipse corresponding to the skull from the reference cross-sectional image. The ultrasound imaging device 600 may measure an angle between the major axis 611 of the cartilage plate 610 of pubic symphysis and the major axis 640 of the ellipse. The ultrasound imaging device 600 may identify the progression direction of the skull and a degree of fetal delivery progress on the basis of the measured angle. The ultrasound imaging device 600 may display information on the progression direction of the skull. The ultrasound imaging device 600 may display information on the degree of fetal delivery progress.

Figure 7:
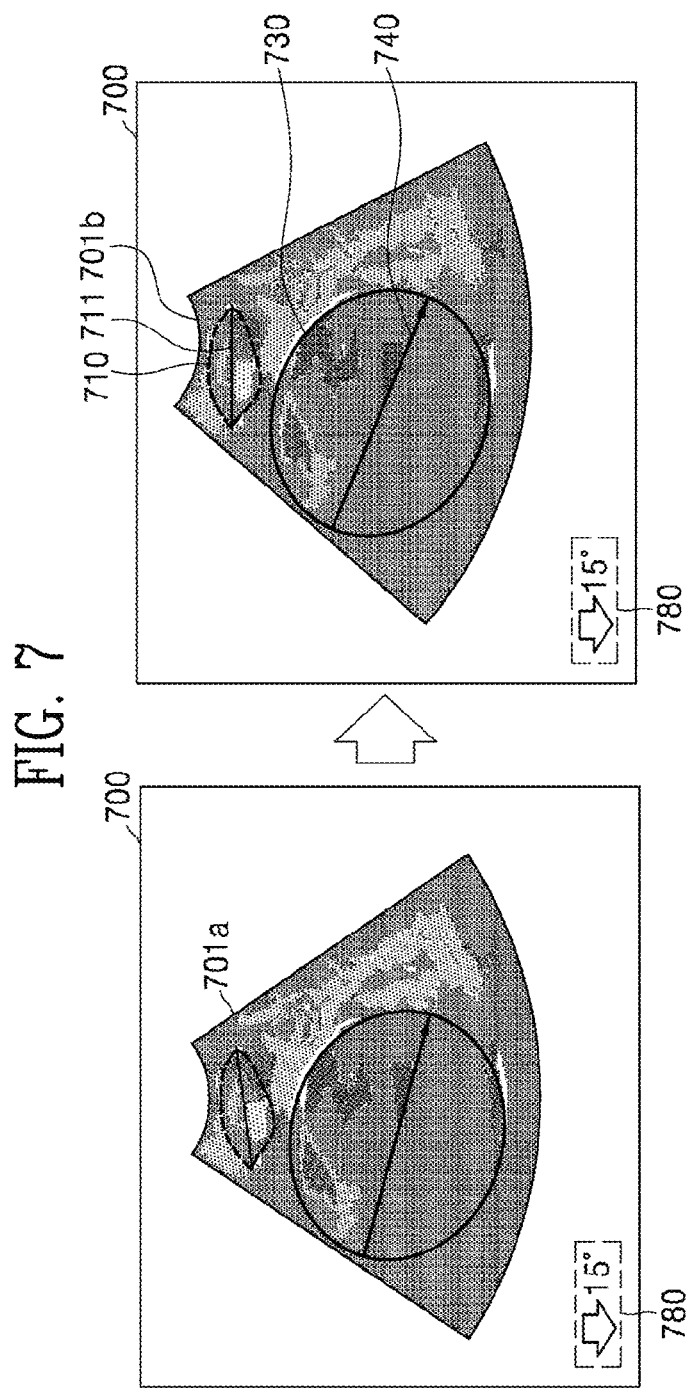
FIG. 7 is a view illustrating a case in which an ultrasound imaging device rotates and displays an ultrasound image, according to an embodiment.

FIG. 7 is a view illustrating a case in which an ultrasound imaging device rotates and displays an ultrasound image, according to an embodiment.

Referring to FIG. 7, an ultrasound imaging device 700 may rotate an ultrasound image 701*a* so that a progression direction of a fetus's skull may be easily indicated, and may display a rotated ultrasound image 701*b*. For convenience of description, the ultrasound image to be rotated is referred to as a first ultrasound image 701*a*, and the rotated ultrasound image is referred to as a second ultrasound image 701*b*.

The ultrasound imaging device 700 may rotate the first ultrasound image 701*a* on the basis of a correspondence relationship between the fetus's skull and an anatomical structure of a mother's body, and may display the second ultrasound image 701*b*.

According to an embodiment, the ultrasound imaging device 700 may rotate the first ultrasound image 701*a* on the basis of a correspondence relationship between a cartilage plate 710 of pubic symphysis of the mother's body and a fetus's skull 730. A user may identify the progression direction of the skull 730 on the basis of an angle at which a major axis 740 of an ellipse is inclined with respect to a major axis 711 of the cartilage plate 710 of pubic symphysis. Accordingly, the ultrasound imaging device 700 may set the major axis 711 of the cartilage plate of pubic symphysis as a reference line, and rotate the first ultrasound image 701*a* such that the major axis 711 of the cartilage plate of pubic symphysis is in a horizontal state. The ultrasound imaging device 700 may display the second ultrasound image 701*b*, which is rotated such that the major axis 711 of the cartilage plate of pubic symphysis is in a horizontal state.

For example, the ultrasound imaging device 700 may rotate the first ultrasound image 701*a* in a clockwise direction such that the major axis 711 of the cartilage plate of pubic symphysis, which is formed in a right upward direction, is in a horizontal state. As another example, the ultrasound imaging device 700 may rotate the first ultrasound image 701*a* in a counterclockwise direction such that the major axis 711 of the cartilage plate of pubic symphysis, which is formed in a right downward direction, is in a horizontal state.

The ultrasound imaging device 700 may set the major axis 740 of the ellipse as a reference line, rotate the ultrasound image such that the major axis 740 of the ellipse is in a horizontal state, and display the rotated ultrasound image. For example, the ultrasound imaging device 700 may rotate the first ultrasound image 701*a* in a clockwise direction such that the major axis 740 of the skull, which is formed in a right upward direction, is in a horizontal state. As another example, the ultrasound imaging device 700 may rotate the first ultrasound image 701*b* in a counterclockwise direction such that the major axis 740 of the skull, which is formed in a right downward direction, is in a horizontal state.

The ultrasound imaging device 700 may display information 780 on an angle at which the major axis 740 of the ellipse is inclined with respect to the major axis 711 of the cartilage plate 710 of pubic symphysis. For example, the ultrasound imaging device 700 may display the direction and degree of the angle at which the major axis 740 of the ellipse is inclined with respect to the major axis 711 of the cartilage plate 710 of pubic symphysis with at least one among symbols, letters, and numerals. In addition, the ultrasound imaging device 700 may display information on an angle at which the second ultrasound image 701*b* is inclined with at least one among symbols, letters, and numerals.

The ultrasound imaging device 700 may display at least one of a plurality of ultrasound images. For example, the ultrasound imaging device 700 may display at least one of the plurality of ultrasound images according to the passage of time on the basis of a time point at which each of the plurality of ultrasound images is obtained.

According to an embodiment, the ultrasound imaging device 700 may rotate at least one of a plurality of first ultrasound images such that the major axis 711 of the cartilage plate 710 of pubic symphysis included in each of the plurality of ultrasound images is in a horizontal state, and may display at least one of a plurality of second ultrasound images.

According to an embodiment, the ultrasound imaging device 700 may rotate at least one of the plurality of first ultrasound images such that the major axis 740 of the skull 730 included in each of the plurality of ultrasound images is in a horizontal state, and may display at least one of the plurality of second ultrasound images.

The user may easily identify the progression direction of the fetus's skull from the second ultrasound image. In addition, the user may easily identify the progression direction of the fetus's skull according to the passage of time from the plurality of second ultrasound images. In addition, the user may easily identify a degree of fetal delivery progress from the progression direction of the fetus's skull, and prepare for fetal delivery.

Figure 8:
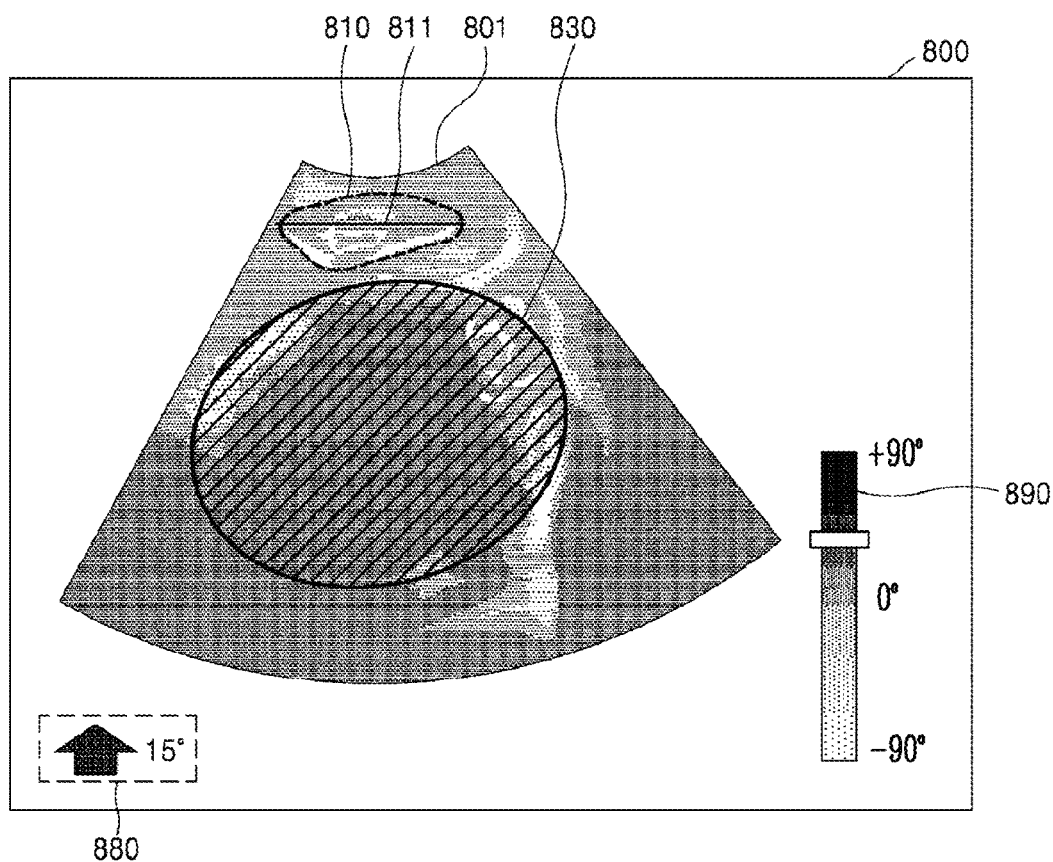
FIG. 8 is a view illustrating a case in which an ultrasound imaging device displays information on a progression direction of a fetus's skull, according to an embodiment.

FIG. 8 is a view illustrating a case in which an ultrasound imaging device displays information on a progression direction of a fetus's skull, according to an embodiment.

Referring to FIG. 8, an ultrasound imaging device 800 may identify a progression direction of a skull 830 on the basis of the progression direction of the fetus's skull 830. The ultrasound imaging device 800 may identify a degree of fetal delivery progress in a mother's body on the basis of the progression direction of the skull 830. The ultrasound imaging device 800 may display information on the degree of fetal delivery progress.

According to an embodiment, the ultrasound imaging device 800 may identify the degree of fetal delivery progress on the basis of an angle between a major axis 811 of a cartilage plate 810 of pubic symphysis and a major axis of an ellipse corresponding to the fetus's skull 830.

For example, when the major axis of the ellipse corresponding to the skull 830 rotates in a clockwise direction by a predetermined angle (e.g., 15°) with respect to the major axis 811 of the cartilage plate 810 of pubic symphysis, the ultrasound imaging device 800 may identify that the progression direction of the skull 830 is a downward direction and may identify the degree of fetal delivery progress as a first degree of fetal delivery progress.

As another example, when the major axis of the ellipse corresponding to the skull 830 rotates in a counterclockwise direction by a predetermined angle (e.g., 0° to 30°) with respect to the major axis 811 of the cartilage plate 810 of pubic symphysis, the ultrasound imaging device 800 may identify that the progression direction of the skull 830 is a horizontal direction and may identify the degree of fetal delivery progress as a second degree of fetal delivery progress.

As still another example, when the major axis of the ellipse corresponding to the skull 830 rotates in a counterclockwise direction by a predetermined angle (e.g., greater than 30°) with respect to the major axis 811 of the cartilage plate 810 of pubic symphysis, the ultrasound imaging device 800 may identify that the progression direction of the skull 830 is an upward direction and may identify the degree of fetal delivery progress as a third degree of fetal delivery progress.

As labor progresses in the mother's body, the major axis of the ellipse corresponding to the skull 830 rotates in a counterclockwise direction with respect to the major axis of the cartilage plate 810 of pubic symphysis. Thus, as the labor progresses from the first degree of fetal delivery progress to the third degree of fetal delivery progress, the fetal delivery is imminent.

The ultrasound imaging device 800 may color-code and display an inside of the ellipse corresponding to the skull 830 with a color corresponding to the identified degree of fetal delivery progress. For example, the color corresponding to the first degree of fetal delivery progress may be green. As another example, the color corresponding to the second degree of fetal delivery progress may be yellow. As still another example, the color corresponding to the third degree of fetal delivery progress may be red.

The ultrasound imaging device 800 may color-code a marker 880 indicating the degree of fetal delivery progress with a color corresponding to the degree of fetal delivery progress, and display the color-coded marker 880. The marker 880 may include symbols, numerals, or letters. The ultrasound imaging device 800 may display a graph 890 indicating the color corresponding to the degree of fetal delivery progress. The ultrasound imaging device 800 may display a marker (e.g., a bar) indicating the color corresponding to the identified degree of fetal delivery progress on the graph 890 in an ultrasound image 801.

A user may easily identify the progression direction of the fetus's skull from the ultrasound image 801 having a color-coded portion. In addition, the user may easily identify the degree of fetal delivery progress from the ultrasound image 801 having a color-coded portion, and prepare for the fetal delivery.

Figure 9:
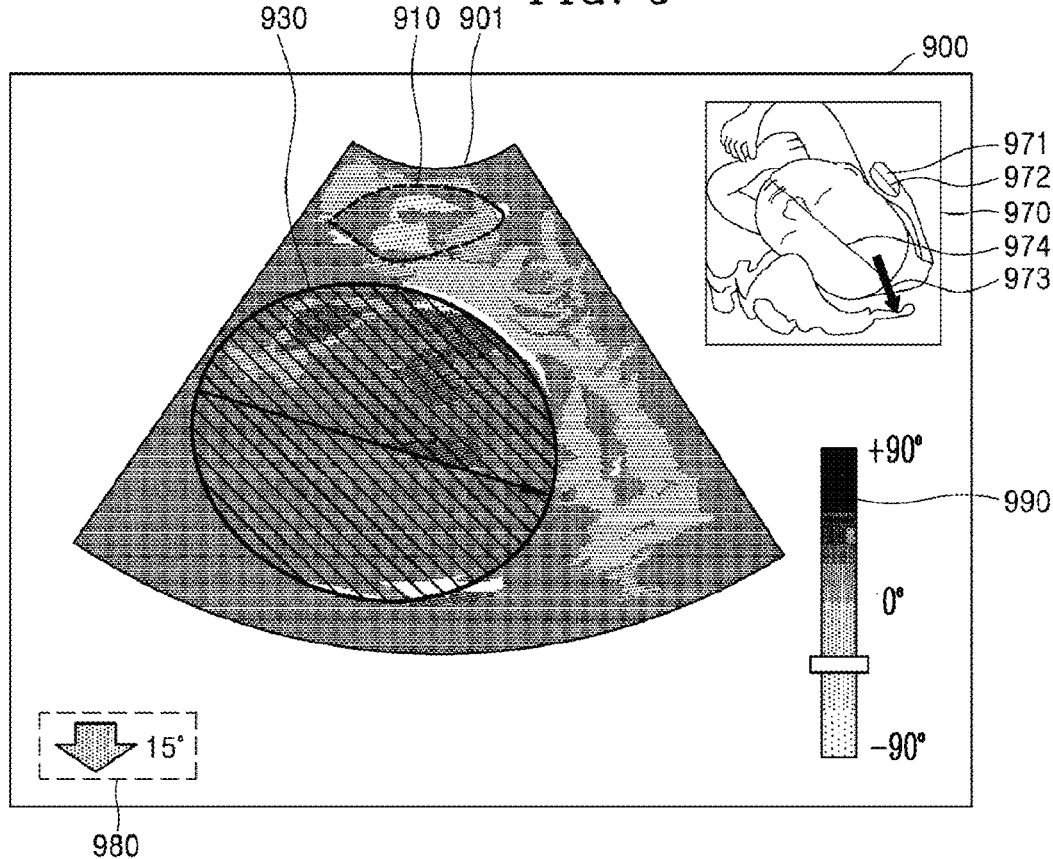
FIG. 9 is a view illustrating a case in which an ultrasound imaging device displays information on a progression direction of a fetus's skull, together with a virtual fetal model image, according to an embodiment.
Figure 10:
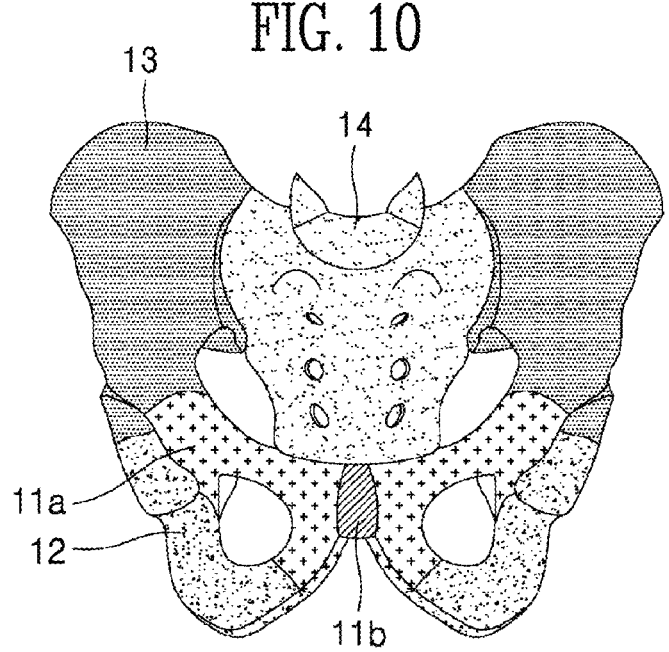
FIG. 10 is a diagram illustrating a structure of a pelvis of a mother's body.

FIG. 9 is a view illustrating a case in which an ultrasound imaging device displays information on a progression direction of a fetus's skull, together with a virtual fetal model, according to an embodiment.

Referring to FIG. 9, an ultrasound imaging device 900 may display a virtual fetal model 970 corresponding to at least one of a progression direction of a skull 930 and a degree of fetal delivery progress that are identified from an ultrasound image 901. Data about the virtual fetal model 970 may be previously stored in a storage unit 150 of the ultrasound imaging device 900.

The storage unit 150 of the ultrasound imaging device 900 may match and store the virtual fetal model with at least one of the progression direction of the skull 930 and the degree of fetal delivery progress. For example, the storage unit 150 of the ultrasound imaging device 900 may store the virtual fetal model corresponding to each of angles between a major axis of a cartilage plate 910 of pubic symphysis and a major axis of an ellipse corresponding to the skull 930.

The ultrasound imaging device 900 may display the virtual fetal model 970 together with the ultrasound image 901. For example, the ultrasound imaging device 900 may display the ultrasound image 901 in a first region of the display unit 140 and display the virtual fetal model 970 in a second region thereof. The virtual fetal model 970 may be at least one of a 2D image and a 3D image generated so that a user may easily identify the degree of fetal delivery progress.

The virtual fetal model 970 may include a general outer shape of a fetus and an anatomical structure of a mother's body. The ultrasound imaging device 900 may display a cartilage plate 971 of pubic symphysis together with the virtual fetal model 970. In addition, the ultrasound imaging device 900 may display a major axis 972 of the cartilage plate 971 of pubic symphysis. The ultrasound imaging device 900 may display a major axis 974 of the fetus's skull on the virtual fetal model 970. The ultrasound imaging device 900 may display the progression direction of the fetus's skull on the virtual fetal model 970. The progression direction of the fetus's skull may be determined by an angle between the major axis 972 of the cartilage plate 971 of pubic symphysis and the major axis 974 of the fetus's skull.

The ultrasound imaging device 900 may represent the degree of fetal delivery progress by displaying the virtual fetal model 970 indicating a relative position of the anatomical structure of the mother's body and the fetus. The ultrasound imaging device 900 may color-code and display an inside of the ellipse corresponding to the skull 930 with a color corresponding to the identified degree of fetal delivery progress, together with the virtual fetal model 970.

The ultrasound imaging device 900 may display a marker 980 indicating the degree of fetal delivery progress, together with the virtual fetal model 970. The marker 980 may include symbols, numerals, or letters. The ultrasound imaging device 900 may display a graph 990 indicating the color corresponding to the degree of fetal delivery progress. The ultrasound imaging device 900 may display a marker (e.g., a bar) indicating the color corresponding to the identified degree of fetal delivery progress on the graph 990 in the ultrasound image 901.

The user may easily identify the progression direction of the fetus's skull from the virtual fetal model 970. In addition, the user may easily identify the degree of fetal delivery progress from the virtual fetal model 970, and prepare for fetal delivery.

Meanwhile, the disclosed embodiments may be implemented through computer-readable recording media having stored therein computer-executable instructions and data. The instructions may be stored in the form of program codes, and when executed by at least one processor, generate a predetermined program module to perform a predetermined operation. Further, when being executed by the processor, the instructions may perform predetermined operations of the disclosed embodiments.

The invention claimed is:

1. A method of generating an ultrasound image by an ultrasound imaging device, the method comprising steps of:
    transmitting an ultrasound signal to an object including a fetus's skull and an anatomical structure of a mother's body;
    receiving an ultrasound echo signal from the object;
    generating ultrasound image data on the basis of the received ultrasound echo signal;
    identifying the fetus's skull and the anatomical structure of the mother's body from the ultrasound image data;
    identifying an angle between the fetus's skull and the anatomical structure of the mother's body;
    identifying a progression direction of the fetus's skull and a degree of delivery progress of the fetus based on the angle; and
    displaying information on the progression direction of the fetus's skull and the ultrasound image, generated based on the ultrasound image data, with a color corresponding to the identified degree of delivery progress of the fetus,
    wherein the identifying the degree of delivery progress of the fetus comprises:
        identifying the degree of delivery progress of the fetus as a first degree, based on the skull being rotated in a clockwise direction by a first predetermined angle with respect to the anatomical structure of the mother's body,
        identifying the degree of delivery progress of the fetus as a second degree, based on the skull being rotated in a counterclockwise direction by a second predetermined angle with respect to the anatomical structure of the mother's body, and
        identifying the degree of delivery progress of the fetus as a third degree, based on the skull being rotated in the counterclockwise direction by a third predetermined angle with respect to the anatomical structure of the mother's body, and
    wherein the first degree corresponds to a first color, the second degree corresponds to a second color, and the third degree corresponds to a third color.

2. The method of claim 1, wherein the anatomical structure of the mother's body is a cartilage plate of pubis symphysis of the mother's body.

3. The method of claim 2, wherein
    the step of identifying the fetus's skull and the anatomical structure of the mother's body from the ultrasound image data includes: steps of identifying a major axis of the cartilage plate of pubis symphysis of the mother's body; identifying an ellipse corresponding to the fetus's skull;

and identifying a major axis of the ellipse, and the step of identifying the progression direction of the fetus's skull and the degree of delivery progress of the fetus includes a step of identifying the progression direction of the fetus's skull and the degree of delivery progress of the fetus on the basis of an angle between the major axis of the cartilage plate of pubis symphysis of the mother's body and the major axis of the ellipse.

4. The method of claim 3, wherein the step of generating the ultrasound image data includes a step of generating a plurality of ultrasound cross-sectional images each including the fetus's skull and the anatomical structure of the mother's body, and the step of identifying the fetus's skull and the anatomical structure of the mother's body includes: steps of identifying the major axis of the cartilage plate of pubis symphysis of the mother's body from each of the plurality of ultrasound cross-sectional images; selecting the ultrasound cross-sectional image having the cartilage plate of pubis symphysis of the mother's body whose major axis is the longest from among the plurality of ultrasound cross-sectional images; and identifying the ellipse corresponding to the fetus's skull and the major axis of the ellipse from the selected cross-sectional image.

5. The method of claim 3, further comprising a step of displaying a first marker indicating the major axis of the cartilage plate of pubis symphysis and a second marker indicating the major axis of the ellipse.

6. The method of claim 3, further comprising a step of rotating the ultrasound image such that the major axis of the cartilage plate of pubis symphysis is in a horizontal state, and displaying the rotated ultrasound image.

7. The method of claim 1, further comprising a step of:
displaying information on the degree of delivery progress of the fetus.

8. A non-transitory computer-readable recording medium, wherein the recording medium has instructions recorded therein for a computer to perform the method of claim 1.

9. An ultrasound imaging device comprising:

an ultrasound probe configured to transmit an ultrasound signal to an object including a fetus's skull and anatomical structure of a mother's body and receive an ultrasound echo signal from the object;

a processor configured to generate ultrasound image data on the basis of the received ultrasound echo signal, identify the fetus's skull and the anatomical structure of the mother's body from the ultrasound image data, identify an angle between the fetus's skull and the anatomical structure of the mother's body, and identify a progression direction of the fetus's skull and a degree of delivery progress of the fetus based on the angle; and a display configured to display information on the progression direction of the fetus's skull and an ultrasound image, generated based on the ultrasound image data, with a color corresponding to the identified degree of delivery progress of the fetus, wherein the processor is further configured to:
identify the degree of delivery progress of the fetus as a first degree, based on the skull being rotated in a clockwise direction by a first predetermined angle with respect to the anatomical structure of the mother's body, identify the degree of delivery progress of the fetus as a second degree, based on the skull being rotated in a counterclockwise direction by a second predetermined angle with respect to the anatomical structure of the mother's body, and identify the degree of delivery progress of the fetus as a third degree, based on the skull being rotated in the counterclockwise direction by a third predetermined angle with respect to the anatomical structure of the mother's body, and wherein the first degree corresponds to a first color, the second degree corresponds to a second color, and the third degree corresponds to a third color.

10. The ultrasound imaging device of claim 9, wherein the anatomical structure of the mother's body is a cartilage plate of pubis symphysis of the mother's body.

11. The ultrasound imaging device of claim 10, wherein the processor identifies a major axis of the cartilage plate of pubis symphysis of the mother's body, identifies an ellipse corresponding to the fetus's skull, identifies a major axis of the ellipse, and identifies the progression direction of the fetus's skull and the degree of delivery progress of the fetus on the basis of an angle between the major axis of the cartilage plate of pubis symphysis of the mother's body and the major axis of the ellipse.

12. The ultrasound imaging device of claim 11, wherein the processor generates a plurality of ultrasound cross-sectional images each including the fetus's skull and the anatomical structure of the mother's body, identifies the major axis of the cartilage plate of pubis symphysis of the mother's body from each of the plurality of ultrasound cross-sectional images, selects the ultrasound cross-sectional image having the cartilage plate of pubis symphysis of the mother's body whose major axis is the longest from among the plurality of ultrasound cross-sectional images, and identifies the ellipse corresponding to the fetus's skull and the major axis of the ellipse from the selected cross-sectional image.

13. The ultrasound imaging device of claim 11, wherein the display displays a first marker indicating the major axis of the cartilage plate of pubis symphysis and a second marker indicating the major axis of the ellipse.

14. The ultrasound imaging device of claim 11, wherein the display rotates the ultrasound image such that the major axis of the cartilage plate of pubis symphysis is in a horizontal state, and displays the rotated ultrasound image.

15. The ultrasound imaging device of claim 9, wherein the display displays information on the degree of delivery progress of the fetus.

* * * * *